US008105788B2

(12) United States Patent
Clarke et al.

(10) Patent No.: US 8,105,788 B2
(45) Date of Patent: Jan. 31, 2012

(54) MUCOPOLYSACCHARIDOSIS (MPS) DIAGNOSTIC METHODS, SYSTEMS, KITS AND ASSAYS ASSOCIATED THEREWITH

(75) Inventors: Lorne A. Clarke, West Vancouver (CA); Derrick Raymond Randall, Burnaby (CA); Graham Sinclair, Victoria (CA)

(73) Assignee: The University of British Columbia, Vancouver (CA)

( * ) Notice: Subject to any disclaimer, the term of this patent is extended or adjusted under 35 U.S.C. 154(b) by 723 days.

(21) Appl. No.: 12/096,589

(22) PCT Filed: Dec. 8, 2006

(86) PCT No.: PCT/CA2006/002011
§ 371 (c)(1),
(2), (4) Date: Nov. 4, 2008

(87) PCT Pub. No.: WO2007/065273
PCT Pub. Date: Jun. 14, 2007

(65) Prior Publication Data
US 2009/0092996 A1    Apr. 9, 2009

Related U.S. Application Data

(60) Provisional application No. 60/748,210, filed on Dec. 8, 2005.

(51) Int. Cl.
*G01N 33/53* (2006.01)
*G01N 31/00* (2006.01)

(52) U.S. Cl. .......... 435/7.1; 435/4; 435/287.9; 436/501; 436/518; 436/525; 436/529; 436/535; 436/809; 427/287; 427/337; 427/338; 422/50; 530/300; 530/350

(58) Field of Classification Search ........................ None
See application file for complete search history.

(56) References Cited

U.S. PATENT DOCUMENTS

| | | | |
|---|---|---|---|
| 4,816,567 | A | 3/1989 | Cabilly et al. |
| 6,002,067 | A | 12/1999 | Clarke et al. |
| 6,426,208 | B1 | 7/2002 | Kakkis et al. |
| 6,508,986 | B1 | 1/2003 | Anderson et al. |
| 6,670,194 | B1 | 12/2003 | Aebersold et al. |
| 6,677,114 | B1 | 1/2004 | Schneider et al. |
| 6,906,320 | B2 | 6/2005 | Sachs et al. |
| 6,940,065 | B2 | 9/2005 | Graber et al. |

FOREIGN PATENT DOCUMENTS

| | | |
|---|---|---|
| WO | WO-2005/080574 | 9/2005 |
| WO | WO-2006/033974 | 3/2006 |

OTHER PUBLICATIONS

Angenendt et al., Anal. Chem. (2003) 75:4368-4372.
Baldwin et al., Anal. Chem. (2001) 73:1707-1720.
Bertone et al., FEBS J.(2005) 272:5400-5411.
Betts et al., Methods Enzymol. (1999) 309:333-350.
Binnig et al., Phys. Rev. Lett. (1986) 56:930.
Braunlin et al., Pediatric Res. (2006) 59(1):27-32.
Byers et al., Mol. Genet. Metab. (1998) 65:282-290.
Chang et al., Clin. Chem. (2000) 46(2):167-174.
Clackson et al., Nature (1991) 352:624-628.
Clarke et al., Hum Mol. Genet. (1997) 6:503-511.
Engvall et al., Immunochemistry (1971) 8:871-874.
Espina et al., J. Immunological Methods (2004) 290:122-133.
Fumic et al., Paediatria Croatica (2005) 49(3):199-201.
Gallegos-Arreola et al., Arch. Med. Res. (2000) 31:505-510.
Gettins, Chem. Rev. (2002) 102:4751-4804.
Goldsby et al., "Enzyme-Linked Immunosorbent Assay," in: Immunology, 5th edition, W. H. Freeman, New York, 2003, pp. 148-150.
Hage, Clin. Chem. (1999) 45:593-615.
Haskins et al., Ped. Res. (1979) 13:1294-1297.
Haskins et al., Vet Pathol. (1992) 29:112-119.
Hillenkamp and Karas, Methods in Enzymol. (1990) 193:280-295.
Hua et al., Clin. Chem. (1998) 44(10):2094-2102.
Hutchens et al., Rapid Commun Mass Spectrom (1993) 7:576-580.
International Search Report for PCT/CA2006/002011, mailed on Mar. 15, 2007, 3 pages.
Johnsson et al., Anal. Biochem. (1991) 198:268.
Jones et al., Anal. Chem. (1998) 780:1233.
Kohler et al., Nature (1975) 256:495.
Karas et al., Anal. Chem. (1988) 60:2299-2310.
Kononen et al., Nature Medicine (1998) 4:844.
Kurien et al., J. Immunological Methods (2003) 274:1-15.
Laemmli, Nature (1970) 227:680.
Lin et al., Clin. Chim. Acta (2006) 369:29-34.
Liotta et al., Nat. Rev. Genet. (2000) 1:480.
Lueking et al., Drug Discovery Today: Targets (2005) 10:789-794.
Mabe et al., Clin. Chim. Acta (2004) 345:135-140.
Mahalingam et al., Indian J Pediatr. (2004) 71:29-32.
Marks et al., J. Mol. Biol. (1991) 222:581-597.
Medzihradszky et al., Anal. Chem. 72:552-558, Feb. 1, 2000.
Meikle et al., Clin. Chem. (1997) 43(8):1325-1335.
Meikle et al., JAMA (1999) 281:249-254.
Meikle et al., Mol. Genet. Metab. (2006) 88(4):307-314.
Meikle et al., Pediatrics (2004) 114(4):909-916.
Natowicz et al., N Engl. J Med. (1996) 335(14):1029-1033.
Nielsen et al., J. Immunological Methods (2004) 290:107-120.
Neufeld and Muenzer, "The metabolic and molecular basis of inherited disease," 8th edition, Scriver et al., eds., McGraw-Hill, New York, 2005, pp. 3421-3452.
Pang et al., J. Immunological Methods (2005) 302:1-12.
Petricoin et al., J. Nutr. (2003) 133:2476S-2484S.
Pelzer et al., Thromb. Haemost. (1988) 59:101-106.
Ramsey et al., Mol. Genet. Metab. (2004)83(3):231-238.
Randall et al., Mol. Genet. Metab. (2006) 88(3):235-243.
Randall et al., Mol. Genet. Metab. (2008) 94:456-461.
Sands et al., J Clin. Invest. (1994) 93:2324-2331.

(Continued)

*Primary Examiner* — Lisa Cook
(74) *Attorney, Agent, or Firm* — Morrison & Foerster LLP

(57) ABSTRACT

Methods, systems, kits and assays for diagnosing, monitoring or screening for mucopolysaccharidosis (MPS) and methods and systems for assaying test compounds for therapeutic activity are described, whereby MPS marker protein levels are assayed as an indication of MPS.

12 Claims, 3 Drawing Sheets

OTHER PUBLICATIONS

Shevchenko et al., Anal. Chem. (2000) 72:2132-2141.
Shevchenko et al., Electrophoresis (1997) 18:2591-2600.
Simonaro et al., Pediatric Res. (2005) 57(5):701-707.
Spellacy et al., PNAS USA (1983) 80:6091-6095.
Tanaka et al., Thromb Haemost. (2005) 94(4):808-813.
Tang et al., Mass Spectrom (2004) 23:34-44.
Terlato and Cox, Genet. Med. (2003) 5:286-294.
Thompson et al., J Inherit Metab Dis (1992) 15:760-768.
Tollefsen et al., J. Biol. Chem. (1982) 257:2162-2169.
Towbin et al., J. Clin. Chem. Biochem. (1989) 27:495.
Towbin et al., PNAS USA (1979) 76:4350.
Visintin et al., J. Immunological Methods (2004) 290:135-153.
Wraith et al., J. Pediatr. (2004) 144:581-588.
Yalow et al., J. Clin. Invest. (1960) 39:1157-1175.

MUCOPOLYSACCHARIDOSIS (MPS) DIAGNOSTIC METHODS, SYSTEMS, KITS AND ASSAYS ASSOCIATED THEREWITH

CROSS-REFERENCE TO RELATED APPLICATIONS

This application is the national phase of PCT application PCT/CA2006/002011 having an international filing date of 8 Dec. 2006, which claims benefit of U.S. provisional patent application No. 60/748,210 filed 8 Dec. 2005. The contents of the above patent applications are incorporated by reference herein in their entirety.

FIELD OF THE INVENTION

The field of the invention relates to medical diagnostics and experimental assay systems. Particularly, relating to lysosomal storage disorders.

BACKGROUND

Lysosomal storage disorders (LSDs) encompass a group of more than 40 diseases resulting from a variety of enzyme deficiencies. LSDs usually present at an early age and can result in debilitating phenotypes. LSD patients commonly have an accumulation of specific macromolecules within tissues and cells, leading to clinical features including liver and spleen enlargement, neurologic findings such as mental retardation, skeletal dysplasia, opthalomological abnormalities and hematological effects such as granulation and vacuoloation of lymphocytes. Subgroupings of LSDs based on the nature of the macromolecule that accumulates include mucopolysaccharidoses (MPS), gangliosidoses, glycosphingolipidoses, glycoproteinoses, mucolipidoses, leukodystrophies and disorder of neutral lipids.

MPS account for the largest single subgroup of LSDs. The MPS are inherited disorders, resulting from insufficient levels of specific lysosomal enzyme activity, involved in degradation of glycosaminoglycans (GAGs). Accumulation of these undegraded or partially degraded GAGs interferes with the normal function of cells, tissue and organs and affects the normal growth and development of the individual.

The overall prevalence of MPS is estimated at about 1/20,000 (MEIKLE P J et al. (1999) JAMA. 281:249-54). A myriad of mutations have been identified for each of the MPS disorders, making genetic screening by itself inefficient. Genotype/phenotype correlation does exist for some deficiencies. However, the variety of mutations for each deficiency makes this prediction difficult in a considerable proportion of patients (TERLATO N J and COX G F. (2003) Genet. Med. 5:286-294). Initial diagnostic inquiries are based on clinical phenotype presentation, and this may be used to guide selection of further biochemical assays.

Highly specific substrates and assays for enzyme activity have been developed to assist the diagnostic process, but these often require invasive tissue sampling and may be time consuming as cells are cultured to provide sufficient quantity for screening. Furthermore, traditional enzyme assays are generally MPS type specific and are thus not amenable to use for general MPS screening. Also, in very young children specific diagnosis may not be possible until the disease has advanced sufficiently to result in damage that may be irreversible. Even if a definitive diagnosis is made and an effective therapy is initiated as early as possible, the disease may have progressed sufficiently to result in irreversible damage.

Assays for urinary GAGs are known and have been used extensively for screening, diagnosing and monitoring MPS patients. However the levels of urinary GAGs may not correlate with disease severity (BYERS S et al. (1998) Mol. Genet. Metab. 65:282-290; GALLEGOS-ARREOLA M P et al. (2000) Arch. Med Res. 31:505-510; MABE P et al. (2004) Clin. Chim. Acta 345:135-140; MAHALINGAM, K. et al. (2004) Indian J Pediatr. 71:29-32).

Lysosomal proteins have been found at elevated levels in the lysosomes from affected individuals, and are reported as general LSD markers (HUA C T et al. (1998) Clin Chem. 44(10):2094-2102; MEIKLE P J et al. (1997) Clin Chem. 43(8):1325-35).

Additional markers of LSD and MPS would be useful. Particularly, markers that correlate with disease severity.

SUMMARY

This invention is based in part on the surprising discovery that a number of MPS marker proteins are useful as diagnostic markers for MPS on the basis that these proteins have differential expression in MPS subjects (either increased or decreased relative to non-MPS subjects). Furthermore, this invention is based in part on the surprising discovery that HCII levels decrease in MPS subjects relative to non-MPS subjects and HCII-T levels increase in MPS subjects relative to non-MPS subjects.

In accordance with one aspect of the invention, there is provided a method of identifying a compound that promotes glycosaminoglycan (GAG) degradation, including: providing a cell having reduced enzyme activity resulting in accumulation of undegraded or partially degraded GAGs, wherein the enzyme is involved in degrading GAGs; contacting the cell with one or more test compounds; and determining whether there is a relative increase or decrease in MPS marker levels. The method may further include administering the test compound to a test subject. The method may further include use of one or more test compounds for the manufacture of a medicament.

In accordance with another aspect of the invention, there is provided a method of identifying a compound that promotes glycosaminoglycan (GAG) degradation, the method including: providing a mucopolysaccharidoses (MPS) experimental animal having reduced enzyme activity resulting in an accumulation of undegraded or partially degraded GAGs; administering to the experimental animal one or more test compounds; and determining whether there is a relative increase or decrease of MPS marker as a result of the administration of one or more test compounds. The method may further include administering the test compound to a test subject. The method may further include use of one or more test compounds for the manufacture of a medicament.

In accordance with another aspect of the invention, there is provided a system for identifying a compound that promotes glycosaminoglycan (GAG) degradation, the system including: one or more cells having reduced enzyme activity resulting in accumulation of undegraded or partially degraded GAGs, wherein the enzyme is involved in degrading GAGs; one or more test compounds, wherein the one or more test compounds is applied to the one or more cells; and a MPS marker detection assay, operable for determining relative MPS marker levels in the one or more cells to which one or more test compounds have been applied, wherein the MPS marker levels are and indicative of the efficacy of the one or more test compounds to promote GAG degradation. The system may further include administering the test compound to a test subject. The system may further include use of one or more test compounds for the manufacture of a medicament.

In accordance with another aspect of the invention, there is provided a system for of identifying a compound that promotes glycosaminoglycan (GAG) degradation, the system including: one or more mucopolysaccharidoses (MPS) experimental animals having reduced enzyme activity resulting in accumulation of undegraded or partially degraded GAGs, wherein the enzyme is involved in degradation of GAGs; one or more test compounds, for administering to the one or more MPS experimental animals; and a MPS marker detection assay, for determining relative MPS marker levels in a biological sample taken from the one or more MPS experimental animals to which one or more test compounds have been administered, wherein an MPS marker levels are and indicative of the efficacy of the one or more test compounds to promote GAG degradation. The system may further include administering the test compound to a test subject. The system may further include use of one or more test compounds for the manufacture of a medicament.

In accordance with another aspect of the invention, there is provided a system for identifying an individual having mucopolysaccharidoses (MPS), the system including: at least one biological sample from the individual; and a MPS marker detection assay, operable for determining relative MPS marker levels in the at least one biological sample, wherein an MPS marker level is indicative of MPS. The system may further include administering a treatment to the individual.

In accordance with another aspect of the invention, there is provided a method of determining whether an individual is at risk for mucopolysaccharidosis, including: assaying a biological sample from the individual for a MPS marker level; and correlating the MPS marker level in the individual with MPS status. The method may further include administering a treatment to the individual.

In accordance with another aspect of the invention, there is provided a method of determining whether an individual is at risk for mucopolysaccharidosis, including: providing a biological sample from the individual; and determining whether the relative MPS marker level for the sample is representative of MPS. The method may further include administering a treatment to the individual.

In accordance with another aspect of the invention, there is provided a method of identifying MPS treatment candidates, the method including: providing a biological sample from a treatment candidate; assaying for a MPS marker level in the biological sample; and comparing the MPS marker level relative to a control. The method may further include administering a treatment to the treatment candidate where the treatment candidate has one or more MPS markers at a level characteristic of MPS.

In accordance with another aspect of the invention, there is provided a method of identifying MPS treatment candidates, the method including: providing a biological sample from a treatment candidate; assaying for a MPS marker level in the biological sample; and comparing the MPS marker level to MPS marker levels associated with MPS. The method may further include administering a treatment to the treatment candidate where the treatment candidate has one or more MPS markers at a level characteristic of MPS.

In accordance with another aspect of the invention, there is provided a method of determining whether an individual is at risk for mucopolysaccharidosis, including: assaying a biological sample from the individual for a MPS marker level; and correlating the MPS marker level in the individual with MPS status. The method may further include administering a treatment to the individual.

In accordance with another aspect of the invention, there is provided a method of determining whether an individual is at risk for mucopolysaccharidosis, including: obtaining a biological sample from the individual; and determining whether the relative MPS marker level for the sample is representative of MPS. The method may further include administering a treatment to the individual.

In accordance with another aspect of the invention, there is provided a method of identifying MPS treatment candidates, the method including: obtaining a biological sample from a treatment candidate; assaying for a MPS marker level in the biological sample; and comparing the MPS marker level relative to a control. The method may further include administering a treatment to the treatment candidate where the treatment candidate has one or more MPS markers at a level characteristic of MPS.

In accordance with another aspect of the invention, there is provided a method of identifying MPS treatment candidates, the method including: obtaining a biological sample from a treatment candidate; assaying for a MPS marker level in the biological sample; and comparing the MPS marker level to MPS marker levels associated with MPS. An increased HCII-T level may be indicative of MPS. The method may further include administering a treatment to the treatment candidate where the treatment candidate has one or more MPS markers at a level characteristic of MPS.

In accordance with another aspect of the invention, there is provided a diagnostic kit for detecting MPS markers in a biological sample, including: a MPS marker detection assay; and an instruction sheet. The MPS marker may be HCII. The MPS marker may be HCII-T. The MPS marker detection assay may include a capture antibody to thrombin and a detection antibody to heparin cofactor II (HCII). The MPS marker detection assay may include a capture antibody to heparin cofactor II (HCII) and a detection antibody to thrombin. The diagnostic kit may further include a solid-phase substrate for coating with a capture antibody. The solid-phase substrate may be selected from one or more of the group including of: a test strip, micro-titer plate, micro-sphere, and micro-particle. The instruction sheet may include assay protocol and/or information regarding the interpretation of assay results, for example, threshold MPS marker levels and their correlation to MPS status. For example, HCII-T blood serum levels as shown in TABLE 3.

In accordance with another aspect of the invention, there is provided a method of monitoring MPS treatment subjects, the method including: providing a biological sample from a subject; assaying for a MPS marker level in the biological sample; and comparing the MPS marker level relative to a control.

In accordance with another aspect of the invention, there is provided a method of monitoring MPS treatment subjects, the method including: providing a biological sample from a subject; assaying for a MPS marker level in the biological sample; and comparing the MPS marker level to MPS marker levels associated with MPS.

In accordance with another aspect of the invention, there is provided a method of monitoring MPS treatment subjects, the method including: obtaining a biological sample from a subject; assaying for a MPS marker level in the biological sample; and comparing the MPS marker level relative to a control.

In accordance with another aspect of the invention, there is provided a method of monitoring MPS treatment subjects, the method including: obtaining a biological sample from a subject; assaying for a MPS marker level in the biological sample; and comparing the MPS marker level to MPS marker levels associated with MPS.

The enzyme may be a lysosomal enzyme. For example, the lysosomal enzyme may be selected from: alpha-L-Iduronidase; Iduronate sulfatase; Heparan-N-sulfatase; N-Acetyl-alpha-glucosaminidase; Acetyl-CoA: alpha-glucosaminide N-acetyltransferase; N-Acetylglucosamine-6-sulfate sulfatase; N-Acetylgalactosamine-6-sulfate sulfatase; Beta-Galactosidase; Arylsulfatase B; Beta-Glucuronidase; and Hyaluronidase. The glycosaminoglycan (GAG) may, for example, include keratin sulfate, chondroitin 6-sulfate accumulation, hyaluronan, heparan sulfate and dermatan sulfate.

The MPS marker may be selected from one or more of the following markers: Fibrinogen, γ-polypeptide; Fibrinogen, α-polypeptide; α-1-antitrypsin 1-5; Inter-α trypsin inhibitor, heavy chain 1; Apolipoprotein B; Pregnancy Zone Protein (Pzp); Gelsolin; Kininogen precursor; Histidine-rich glycoprotein; Alpha-1 proteinase inhibitor 2; Apolipoprotein C-III; Factor XIII beta; Paraoxonase 1; and Heparin cofactor II (HCII-T). The MPS marker may be HCII. The MPS marker may be HCII-T.

MPS may be selected from one or more of the following types: MPS I (MPS IH/MPS IH/S/MPS IS); MPS II (severe and attenuated); MPS III (A, B, C and D); MPS IV (type A and type B); MPS VI; MPS VII; and MPS IX.

The one or more test compounds may result in an increase in HCII levels as a positive response to the test compound. The one or more test compounds may result in a decrease in HCII-T levels as a positive response to the test compound. A positive response to a test compound may be representative of one or more of the following: an indication of glycosaminoglycan (GAG) degradation in a subject; an increase in lysosomal enzyme function; and an improved MPS phenotype. A test compound may promote GAG degrading enzyme activity or itself may degrade GAGs or both. Furthermore, a test compound may include a gene therapy delivery vector, which for example may encode an active lysosomal enzyme to compensate for the defective lysosomal enzyme in a subject with MPS.

An assay for a MPS marker detection or marker level detection may be selected from one or more of the following: immunoquantification; chromatography; enzyme-linked imunosorbent assay (ELISA); Western blotting; and mass spectroscopy; or other protein fragment, protein and protein complex detection methods described herein. MPS detection may be performed by a reflectance or electrochemical measurement system. An increase or decrease in MPS marker levels may be relative to a positive or negative control or as compared to a predetermined threshold (for example, HCII-T levels set out in TABLE 3). An increased HCII-T or decreased HCII (MPS marker) level may be indicative of MPS.

A biological sample may be selected from one or more of the following cells, blood, serum, plasma, muscle, bone, neurological tissue, saliva, urine, mucus or other sample acquired in biopsy. Biological samples for HCII or HCII-T testing may be selected from blood, serum, plasma, tissues, cells and cerebral spinal fluid (CSF). A biological sample may be collected prior to MPS treatment, during MPS treatment, following MPS treatment or any combination thereof. Biological sample collection may occur in prenatally, postnatally, during childhood and during adulthood.

A test subject or treatment subject may be a patient undergoing clinical trial with an experimental MPS treatment or an existing MPS treatment.

The MPS marker may be HCII. A decreased HCII level may be indicative of MPS. The MPS marker may be HCII-T. An increased HCII-T level may be indicative of MPS. Where the MPS marker is HCII-T or HCII, the MPS may be selected from the following MPS I, MPS II, MPS III, MPS VI and MPS VII. MPS treatment may include aldurazyme administration where the MPS is MPS I. The MPS treatment may include a bone marrow transplant. A subject's MPS status may be classified as non-MPS where they have a HCII-T serum level of 0-12,000 pM, as possible MPS where they have a HCII-T serum level of 12,001-16,999 pM and MPS positive where they have a HCII-T serum level of 17,000-600,000 pM. Alternatively, a subject may be classified as non-MPS where they have a HCII-T serum level of 0-13,000 pM, as possible MPS where they have a HCII-T serum level of 13,001-15,999 pM and MPS positive where they have a HCII-T serum level of 16,000-600,000 pM. Alternatively, a subject may be classified as non-MPS where they have a HCII-T serum level of 0-14,000 pM, as possible MPS where they have a HCII-T serum level of 14,001-14,999 pM and MPS positive where they have a HCII-T serum level of 15,000-600,000 pM. Alternatively, a subject may be classified as non-MPS where they have a HCII-T serum level of 0-15,000 pM and MPS positive where they have a HCII-T serum level of 15,001-600,000 pM. Alternatively, a subject may be classified as non-MPS where they have a HCII-T serum level of 0-14,000 pM and MPS positive where they have a HCII-T serum level of 15,000-600,000 pM. Alternatively, a subject may be classified as non-MPS where they have a HCII-T serum level of 0-13,500 pM and MPS positive where they have a HCII-T serum level of 16,000-600,000 pM.

Other aspects and features of the present invention will become apparent to those ordinarily skilled in the art upon review of the following description of specific embodiments of the invention in conjunction with the accompanying figures.

DETAILED DESCRIPTION

1. Definitions

Figure 1A:
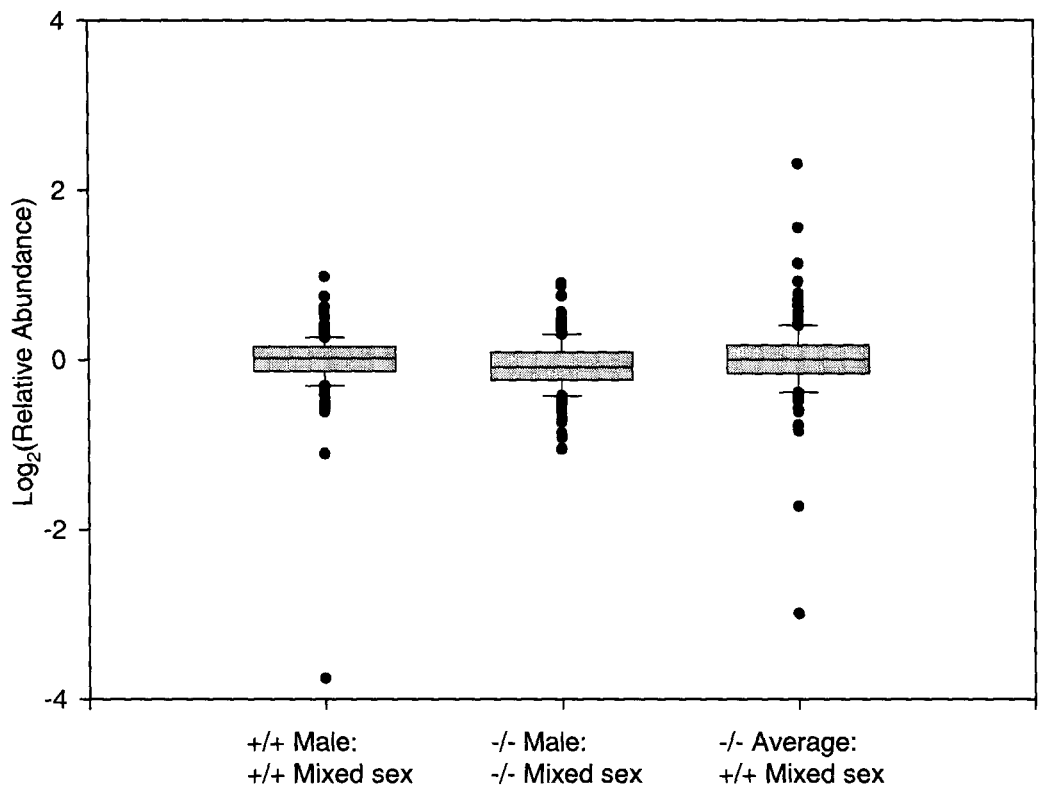
FIG. 1A show box plots of relative abundances for proteins identified with 99% confidence in each sample pool relative to controls. Grey boxes cover the interquartile range, whiskers extend to $10^{th}$ and $90^{th}$ centiles, and individual points indicate the outliers.
Figure 1B:
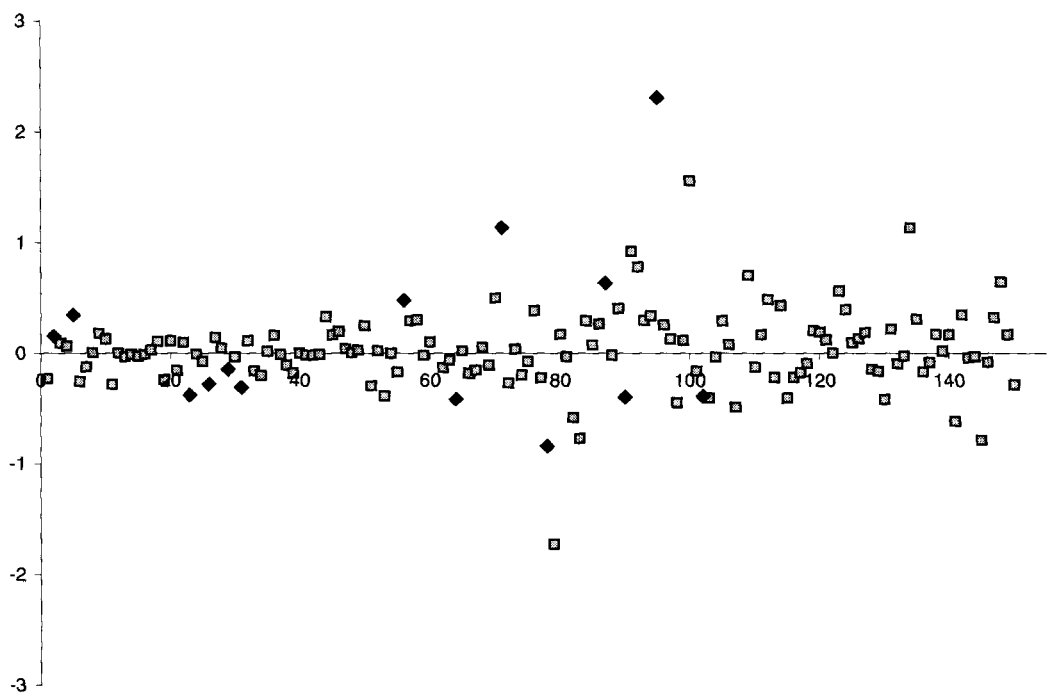
FIG. 1B is a logarithmic plot of average relative abundance of proteins in Idua−/− pools vs. Idua+/+ mixed sex, ≧99% confidence, with proteins rank ordered from left to right based on descending Protein % Confidence score. Dashed lines indicate a two-fold increase or decrease in the average relative abundance of a protein present in the Idua−/− pools compared to the Idua+/+ mixed sex pool. Proteins represented by squares (♦) have significant changes in relative abundance and are listed on TABLE 2 below.

An "antibody", as used herein, includes polyclonal antibodies from any native source, and native or recombinant monoclonal antibodies of classes IgG, IgM, IgA, IgD, and IgE, hybrid derivatives, humanized or chimeric antibodies, and fragments of antibodies including Fab, Fab', and F(ab')2, and the products of a Fab or other immunoglobulin expression library.

An "epitope", as used herein, refers to an arrangement of amino acids in a protein or modifications thereon (for example glycosylation). The amino acids may be arranged in a linear fashion, such as a primary sequence of a protein, or may be a secondary or tertiary arrangement of amino acids in close proximity once a protein is partially or fully configured. Epitopes may be specifically bound by an antibody, antibody fragment, peptide, peptidomimetic or the like, or may be specifically bound by a ligand. An epitope may have a range of sizes—for example a linear epitope may be as small as two amino acids, or may be larger, from about 3 amino acids to about 20 amino acids. In some embodiments, an epitope may be from about 5 amino acids to about 10 or about 15 amino acids in length. An epitope of secondary or tertiary arrangements of amino acids may encompass as few as two amino acids, or may be larger, from about 3 amino acids to about 20 amino acids. In some embodiments, a secondary or tertiary epitope may be from about 5 amino acids to about 10 or about 15 amino acids in proximity to some or others within the epitope.

A "glycosaminoglycan" (GAG) is a long, unbranched polysaccharide molecule, composed of repeating disaccharide units. The first sugar residue in the repeating disaccharide is an amino sugar, such as N-acetylglucosamine or N-acetylgalactosamine, and is usually sulfated. The second sugar residue is a uronic acid, such as glucuronic or iduronic acid. Four groups of GAGs include: (a) hyaluronan; (b) chondroitin sulfate and dermatan sulfate; (c) heparan sulfate and heparin; and (d) keratin sulfate. GAGs may be covalently linked to proteins in the form of proteoglycans, and are major structural components of connective tissue such as cartilage, and of the cornea of the eye. An alternate term for a "glycosaminoglycan" is a "mucopolysaccharide".

"Mucopolysaccharidosis" (MPS) refers to a subgroup of lysosomal storage disorders (LSD). MPS are characterized by the accumulation and storage of GAG within lysosomes. An MPS phenotype refers to the clinical signs or symptoms of an MPS in a subject. The clinical signs or symptoms may be varied, depending on the severity and specific MPS disorder.

MPS IH (Hurler syndrome) is an autosomal recessive disorder resulting from numerous different mutations of alpha-L-idurondase, which result in deficiencies of the enzyme. Progressive mental retardation, hepatosplenomegaly, skeletal malformations and cardiopulmonary compromises typically lead to death in the first decade. Affected individuals appear normal at birth, with the characteristic appearance and accelerated growth developing in the first year. Clinical diagnosis may be suggested in the first 2 years by, for example, hepatosplenomegaly, corneal clouding, coarse features and joint problems. Developmental delay is observed between the first and second years, with subsequent slow mental development and/or regression. Additional complications of this disorder include hearing loss, chronic respiratory infections, valvular heart disease and brain ventricular enlargement.

MPS IS (Scheie syndrome) and MPS IH/S (Hurler/Scheie syndrome) are less severe variants of MPS IH and also involve an alpha-L-idurondase deficiency. MPS IS subjects may survive into late adulthood, although severe progressive skeletal disease that resembles osteoarthritis is observed. Normal intelligence is also found. MPS IH, MPS IH/S and MPS S are collectively sometimes referred to herein as MPS I.

MPS II (Hunter syndrome) is an X-linked recessive disorder resulting from mutations of iduronate sulfatase, which result in deficiencies of the enzyme. Clinical manifestations of MPS II range from severe CNS and involvement of the viscera with death in late childhood, to attenuated forms having normal CNS function and survival into adulthood.

MPS III A, B, C and D (Sanfilippo syndromes) are autosomal recessive disorders resulting from various enzyme deficiencies (i.e. glucosamine-N-sulfatase or heparan N-sulfatase; alpha-N-acetylglucosaminidase; acetyl CoA:alpha-glucosaminide-N-acetyltransferase; and N-acetylglucosamine 6-sulfatase, respectively). Skeletal defects and hepatosplenomegaly are less pronounced than in MPS I and II. However, progressive behavioural problems, mental retardation and seizures are observed. Affected subjects may survive into early to mid-adulthood.

MPS IV (Morquio syndrome) is an autosomal recessive disorder characterized by deficiency in a N-acetylgalactosamine-6-sulfatase or a galactose-6-sulfatase deficiency in type A or a beta-galactosidase deficiency in type B. Type A presents the more clinically severe skeletal disease, Extreme shortening of the trunk may occur due to vertebral collapse, and joint laxity may lead to osteoarthritis-like damage of the joints. Paralysis may also result from instability of the upper cervical spine compressing the spinal cord. Mitral valve insufficiencies may also be present.

MPS VI (Maroteaux-Lamy syndrome) is an autosomal recessive disorder resulting from a deficiency of the arylsulfatase B enzyme (N-acetylgalactosamine-6-sulfatase). The general phenotype resembles MPS IH, although it may be clinically variable. Intelligence is normal and life span may last to early to mid-adulthood. Valvular disease and progressive pulmonary hypertension may be present and may be a frequent cause of death.

MPS VII (Sly syndrome) is an autosomal recessive disorder resulting from a beta-glucuronidase deficiency. Clinical symptoms include mental retardation, short stature, skeletal dysplasia, hepatosplenomegaly. Survival into adulthood may occur in milder cases, with osteoarthritis-like joint complications common.

MPS IX results from a hyaluronidase deficiency, which results in the accumulation of hyaluronan (NATOWICZ M R. et al. N Engl J Med. (1996) 335(14):1029-33).

MPS type designations MPS V and MPS VIII are no longer used.

The MPS types share many clinical features with varying degrees of severity and phenotypic effects. TABLE 1 lists the MPS disorders, their specific enzyme deficiency and the GAG stored in the lysosome as a result of the enzyme deficiency.

TABLE 1

Mucopolysaccharidoses and the respective enzyme deficiency and stored glycosaminoglycan. Syndrome name is shown in brackets.

| MPS TYPE | Enzyme Deficiency | Stored Material |
|---|---|---|
| MPS I H, (Hurler) | alpha-L-Iduronidase | Dermatan sulfate |
| MPS I H/S, (Hurler/Scheie) | | Heparan sulfate |
| MPS I S, (Scheie) | | |
| MPS II (Hunter) | Iduronate sulfatase | Dermatan sulfate Heparan sulfate |
| MPS III A (Sanfilippo A) | Heparan-N-sulfatase | Heparan sulfate |
| MPS III B (Sanfilippo B) | N-Acetyl-alpha-glucosaminidase | Heparan sulfate |

TABLE 1-continued

Mucopolysaccharidoses and the respective enzyme deficiency and stored glycosaminoglycan. Syndrome name is shown in brackets.

| MPS TYPE | Enzyme Deficiency | Stored Material |
|---|---|---|
| MPS III C (Sanfilippo C) | Acetyl-CoA: alpha-glucosaminide N-acetyltransferase | Heparan sulfate |
| MPS III D (Sanfilippo D) | N-Acetylglucosamine-6-sulfate sulfatase | Heparan sulfate |
| MPS IV A (Morquio) | N-Acetylgalactosamine-6-sulfatesulfatase | Keratan sulphate Chondroitin-6 sulfate |
| MPS VI B (Morquio) | Beta-Galactosidase | Keratan sulphate |
| MPS VI (Maroteaux-Lamy) | Arylsulfatase B | Dermatan sulfate |
| MPS VII (Sly) | Beta-Glucuronidase | Dermatan sulphate Heparan sulfate |
| MPS IX | Hyaluronidase | Hyaluronan |

Other examples of clinical signs or symptoms of an MPS will be known to a physician having experience in treating MPS. Alternatively, a more detailed description of the clinical signs or symptoms may be found in, for example NEUFELD E F. and MUENZER J. "The metabolic and molecular basis of inherited disease" 8th edition, C R SCRIVER et al. editors. McGraw-Hill, NY 2005. pp 3421-3452.

As used herein, an "MPS marker" refers to a marker that is associated with the MPS in a subject. The MPS marker may be one or more protein(s), a complex of a protein with another molecule, such as an oligosaccharide or GAG, a protein complex (for example HCII-T) or a protein fragment. Such a marker may be present at a greater or at a lesser level (for example see TABLE 2) than in a subject unaffected with an MPS (a 'non-MPS' subject). The MPS marker may be associated with the onset of the clinical phenotype of the MPS, or may be detectable before clinical onset of any MPS phenotype. Examples of MPS markers may be selected from any one or more of the differentially expressed proteins identified in the mouse MPS model described herein (alone, in combination or complexed with another entity), as compared to wild type mice as follows: fibrinogen, γ-polypeptide; Fibrinogen, α-polypeptide; α-1-antitrypsin 1-5; Inter-α trypsin inhibitor, heavy chain 1; Apolipoprotein B; Pzp protein; Gelsolin; Kininogen precursor; Histidine-rich glycoprotein; Alpha-1 proteinase inhibitor 2; Apolipoprotein C-III; Factor XIII beta; Paraoxonase 1; and Heparin cofactor II.

A "sample" or a "biological sample" refers to a quantity of tissue or body fluid which may be obtained from a subject having, suspected of having or not having MPS. Samples may be obtained, for example, by curettage, needle aspiration biopsy or needle (core) biopsy, incisional biopsy for sampling of tissue at a specific site, or by excisional biopsy. Samples may include one or more of the following: cells, blood, serum, plasma, muscle, bone, neurological tissue, saliva, urine, mucus or other sample acquired in biopsy. Samples such as blood, saliva, urine, mucus, etc may be collected using methods known in the art. For example, biological samples for HCII or HCII-T testing may be selected from blood, serum, plasma, tissues, cells and cerebral spinal fluid (CSF).

As used herein, a "SERPIN" is a member of the serine protease inhibitor super-family of proteins. SERPINs specifically inhibit serine proteases as part of the regulation of various metabolic pathways in living cells and whole organisms (for example the coagulation system). Examples of SERPINs include: antithrombin III (ACIII); heparin cofactor II (HCII); Protein C inhibitor (PAI-3); Glia-derived nexin (PN1); pigment epithelium-derived factor (PEDF); and alpha$_1$-proteinase inhibitor (α-PI). SERPIN regulation of protease activity is described in GETTINS P G. Chem Rev. (2002) 102:4751-4804. SERPIN protease complex formation is essentially irreversible and causes a dramatic structural change in the protease leading to its inactivity. The HCII-T complex, for example, is subsequently recognized by specific receptors and degraded in the liver.

A "subject" as used herein refers to an animal, such as a mammal. A subject may be a mouse, or other experimental animal such as a cat, or may refer to a human (a 'patient'). A human subject may be diagnosed with an MPS, suspected of having an MPS, may be undiagnosed or be known not to have MPS. The mouse or other experimental animal may be 'wild-type', or may be a transgenic animal or have a chemically induced MPS phenotype. Examples of transgenic mouse models for LSDs include those described in WO 2005/080574 or U.S. Pat. No. 6,002,067. A "normal" or "control" or "unaffected" or "non-MPS" subject refers to a subject that does not have MPS.

2. General Description

In view of the potential limitations of existing MPS detection methods, the present application demonstrates a proteomics approach of identifying differentially expressed proteins in a mouse model system (see Example 1 below). Fourteen differentially expressed proteins were identified (see TABLES 2 and 8A) all having either an increased or decrease expression in the MPS mouse model relative to the wild type mouse. Accordingly, all 14 proteins are useful as MPS markers suitable for diagnostic screening of subjects for MPS (see TABLE 2 and 8A/8B) by comparing the levels of MPS marker relative to a control (either positive or negative) or against a known range of absolute values representing MPS patients and non-MPS patients. Alternatively, these differentially expressed proteins may be used as MPS markers to detect a response to a test compound in a MPS assay system as described herein. The present proteomics approach was further validated with additional and more detailed testing of heparin co-factor II (HCII), wherein immunologic testing of a variety of MPS subjects showed a decrease in HCII and a corresponding increase in HCII-T complex formation. Accordingly, either an HCII decrease or an increase in HCII-T complex formation is demonstrated as a marker for MPS (see examples below). The below examples also demonstrate that HCII-T and HCII detection are capable of distinguishing between phenotypic variants of MPS types and subtle changes in response to treatment regiments. Accordingly, MPS markers are useful in monitoring a subject's response to therapy or to detect a response to a test compound during the administration of a therapeutic course. Furthermore, MPS markers are useful in diagnostic screening of subjects for MPS as described herein. Such a diagnostic may be used both prenatally and postnatally, during childhood or in adulthood as required. The result of a positive diagnostic test for MPS may be used to decide, for example, whether further testing is needed or what type of treatment is appropriate. Additionally, a positive diagnostic test for MPS would be useful to identify subjects with MPS prior to developing a clinical phenotype, which may be representative of cell damage due to GAG accumulation. The earlier that treatment is started, the more likely that the treatment will be effective in minimizing damage.

Furthermore, the differentially expressed proteins may be used as markers for MPS to assay for the effectiveness of a test compound in a screening system. Such a system may utilize an animal model or cell line or a cell free system as described herein. Animal models are known in the art, for example:

MPS I, VI and VII feline (MPS I and VI) and canine (MPS VII) models HASKINS M E. et al. Vet Pathol (1992) 29:112-119;

MPS I feline and canine models HASKINS M E. et al. Ped. Res. (1979) 13:1294-1297 and SPELLACY et al. Proc. Nat'l. Acad. Sci. (USA) (1983) 80:6091-6095;

MPS IIID goat model THOMPSON J N. et al. J Inherit Metab Dis (1992) 15:760-768;

MPS VII mouse model SANDS M S. et al. J Clin Invest (1994) 93:2324-31;

MPS Model where experimental animal is given Intimatan (dermatan 4,6-O-disulfate) (TANAKA K A. et al. Thromb Haemost. (2005) 94(4):808-13.);

MPS I mouse model CLARKE L A. et al. Hum Mol Genet. (1997) 6:503-511; and

U.S. Pat. No. 6,002,067 and PCT/CA.2005/000266.

Similarly, MPS cell lines are known in the art, for example: MEIKLE P J. et al. Clinical Chemistry (1997) 43(8):1325-1335 at 1327 and 1329 SF 1779 (MPS II), SF 3168 (MPS VI), SF 850 (MPS IVA), SF 1770 (MPS IVA), SF 486 (MPS IIIA), SF 737 (MPS IIIA), SF 913 (MPS VI), and SF 3223 (MPS VI).

Test compounds may be selected, for example, from combinatorial compound libraries; potential replacement enzymes, analogues or derivatives thereof; cell therapies (such as bone marrow transplant or stem cell transplants etc.); or gene therapies. The methods described herein may also be useful to monitor a subject's response to a known therapeutic or to test the efficacy of unknown therapeutics.

The assaying of test compounds may be performed for example though the addition of one or more a test compounds to a MPS cell system or through the administration of a one or more a test compounds to an MPS animal model, with subsequent MPS marker detection at various intervals both prior to addition/administration of the test compound and at various intervals following addition/administration to determine the relative levels of one or more MPS markers. For example, a decrease in HCII-T complex would suggest that the test compound may have a desirable activity in the assay and subsequent potential as a treatment for MPS. HCII-T detection may be by ELISA or any one or more of the other detection methods described herein.

Glycosaminoglycan (GAG) Degradation

The deficient enzymes in the various MPS (see TABLE 1) are part of a highly ordered degradation pathway for GAGs. Generally, the long chain GAG is cleaved into smaller fragments by endoglucuronidases or endohexosaminidases, and the individual monosaccharides subsequently removed by specific enzymes. It is these specific enzymes that are deficient in the various MPS types. Details of the pathways for degradation of specific GAGs, including the enzymes involved at each step and the substrates of each may be found in, for example, "Essentials of Glycobiology, A. VARKI, R. CUMMINGS I. eds. (1999) Cold Spring harbor Laboratory Press, Cold Spring Harbor, N.Y.

Currently Used Diagnosis Methods for MPS

Clinical phenotypes of MPS may not be evident at birth, but often appear within a few months of birth, or as late as several years of age. During infancy and childhood, physical and mental development may be affected or delayed. Clinical symptoms such as short stature, bony dysplasia, hirsutism may be observed, as well as more characteristic facies of the MPS disorders, such as thick lips, open mouth or flattened nasal bridge. Depending on the specific MPS, mental retardation may also be present. The specific clinical phenotype of each specific MPS will be known to a physician versed in the art, and may be found in, for example "The Merck Manual of Diagnosis and Therapy" 17th edition. M H BEERS and R BERKOW, editors. 1999-2005, Merck & Co. NEUFELD E F. and MUENZER J. In The metabolic and molecular basis of inherited disease 8th edition, C R SCRIVER et al. editors. McGraw-Hill, NY 2001. pp 3421-3452.

With the exception of MPS II, which is X-linked, all the MPS disorders are autosomal recessive. A wide variety of mutations, including point mutations, insertions, deletions and polymorphisms are observed and affected individuals may be heterozygous for their specific mutations—each parent contributing a different defective copy of the gene. Some correlation exists between the severity of the MPS and the specific mutation, but this may not be practical for widespread use as a diagnostic, given the heterogeneous genetic makeup of the MPS affected population.

Diagnosis of specific MPS may be made using a combination of observed clinical phenotype, urinary analysis for GAGs and enzyme assays (for example, MPS I results from a deficiency of the enzyme α-L-iduronidase (IDUA; EC 3.2.1.76) (NEUFELD supra). IDUA deficiency results in abnormalities in the degradation of the glycosaminoglycans (GAGs) heparan sulphate and dermatan sulphate, which subsequently accumulate in the lysosome. Severity of the disorder is estimated subjectively, based on clinical phenotype.

Therapies for MPS

Few treatment options exist for subjects affected with MPS. Supportive therapy and/or palliative care may be offered largely to improve quality of life of the subject. With each MPS disorder, supportive management of the clinical manifestations is provided. For example, patients presenting with chronic respiratory complications would be treated for the frequent infections and congestion of the chest and airway, but the underlying cause (the buildup of the GAG in the lysosome) cannot be addressed in this manner.

Bone marrow transplantation is a therapeutic option for some MPS subjects, although the efficacy of this procedure varies with the severity of the disease and is often limited to subjects who are strong enough to endure the procedure.

Enzyme replacement therapy (ERT) has been shown to be a useful therapeutic approach in some MPS subjects. For example, in MPS I affected subjects, clinical studies have demonstrated that administration of recombinant alpha-L-iduronidase (ALDURAZYME™; U.S. Pat. No. 6,426,208) can alter the phenotype of MPS I patients to varying degrees (WRAITH J E. et al. (2004) Enzyme replacement therapy for mucopolysaccharidosis I: a randomized, double-blinded placebo-controlled, multinational study of recombinant human alpha-L-iduronidase (laronidase) J. Pediatr. 144: 581-588). There are also ERT clinical trials for MPS II and MPS VI and as therapies are developed the need for early diagnosis will become greater.

Monitoring of Disease Progress or Therapeutic Efficacy

The progress of MPS may be monitored by the alterations in clinical phenotypes and analysis of urinary GAGs may provide some guidance, but does not necessarily correlate with disease severity. Additionally, enzymatic activity assays may be useful in confirming MPS, but are unlikely to be useful in broad based screening or for patient monitoring.

A MPS marker as described herein may be used to diagnose MPS in a subject, monitor disease severity and response to therapy (see TABLE 2 below).

Differentially Expressed Proteins in MPS Relative to Controls

TABLE 2

| Protein | Protein Abundance in MPS |
|---|---|
| Fibrinogen, γ-polypeptide | Elevated protein levels in MPS |
| Fibrinogen, α-polypeptide | Elevated protein levels in MPS |
| α-1-antitrypsin 1-5 | Elevated protein levels in MPS |

TABLE 2-continued

| Protein | Protein Abundance in MPS |
| --- | --- |
| Inter-α trypsin inhibitor, heavy chain 1 | Elevated protein levels in MPS |
| Apolipoprotein B | Elevated protein levels in MPS |
| Pzp protein | Elevated protein levels in MPS |
| Gelsolin | Decreased protein levels in MPS |
| Kininogen precursor | Decreased protein levels in MPS |
| Histidine-rich glycoprotein | Decreased protein levels in MPS |
| Alpha-1 proteinase inhibitor 2 | Decreased protein levels in MPS |
| Apolipoprotein C-III | Decreased protein levels in MPS |
| Factor XIII beta | Decreased protein levels in MPS |
| Paraoxonase 1 | Decreased protein levels in MPS |
| Heparin cofactor II | Decreased protein levels in MPS |

Furthermore, levels of heparin cofactor II (HCII) and alternatively levels of heparin cofactor II-thrombin (HCII-T) complex may be measured in MPS patients as described below. Serum HCII-T levels are elevated well beyond that seen in control serum samples and provide a marker of MPS disease as shown below in TABLE 3. Subjects identified as 'Possible MPS' (i.e. 12,001-16,999) may be subjected to further enzyme analysis or genetic analysis to make a determination of the subjects MPS type or to confirm the subject's MPS status. 'Non-MPS' subjects would not need further MPS screening and 'MPS Positive' subjects would also be candidates for further enzyme analysis or genetic analysis to make a determination of MPS type to assist in making decisions regarding treatment options. Alternatively, a MPS marker (for example HCII-T) may be compared to a positive and/or negative control value. The HCII-T serum levels (pM) shown below in TABLE 3 are based on measurements obtained using the ELISA materials and methods described herein. However, the ranges and absolute values may vary, for example, depending on the biological sample tested, sample preparation methods, the protocol used to test for MPS markers, and the MPS marker tested etc. This is demonstrated in part by TABLE 9, whose HCII-T values (pM) were derived using an earlier ELISA protocol (differing in the dilutions used) and also show differences between serum and plasma HCII-T levels in the same subjects.

TABLE 3

| Subject Status | HCII-T Serum Levels (pM) |
| --- | --- |
| Non-MPS | 0-12,000 |
| Possible MPS | 12,001-16,999 |
| MPS Positive | 17,000-600,000 |

Protein Fragment, Protein and Protein Complex Detection

Proteins or protein complexes may be specifically identified and quantified by a variety of methods known in the art and may be used alone or in combination. Immunologic- or antibody-based techniques include enzyme-linked immunosorbent assay (ELISA), western blotting, immunofluorescence, some chromatographic techniques (i.e. immunoaffinity chromatography), and the like, and are based on the specificity of an antibody or antibodies for a particular epitope or combination of epitopes associated with the protein or protein complex of interest.

Non-immunologic methods include those based on physical characteristics of the protein or protein complex itself. Examples of such methods include electrophoresis, some chromatographic techniques (i.e. high performance liquid chromatography (HPLC), fast protein liquid chromatography (FPLC), ion exchange chromatography, size exclusion chromatography and the like), mass spectrometry, sequencing, protease digests, and the like, and are based on the mass, charge, hydrophobicity or hydrophilicity, and the amino acid complement of the protein or protein complex, and the specific sequence of the amino acids.

Additionally, immunologic and non-immunologic methods may be combined to identify or characterize a protein or protein complex.

Antibodies or fragments of antibodies may be generated by any of several methods or techniques known in the art. Such methods or techniques may be described in, for example, HARLOW and LANE, Antibodies: A Laboratory Manual, Cold Spring Harbour, N.Y. (1989) or COLIGAN et al. eds. Current Protocols in Immunology, John Wiley & Sons, New York, N.Y. (1992-2006) or HARLOW and LANE, Using Antibodies: A Laboratory Manual. Cold Spring Harbor Laboratory Press, New York.

A hybridoma method may be used to make monoclonal antibodies (KOHLER et al. (1975) Nature 256:495). Alternately, monoclonal antibodies may be made by recombinant DNA methods (for example U.S. Pat. No. 4,816,567). Monoclonal antibodies may also be isolated from a phage antibody library, for example, by using the techniques described in CLACKSON et al. (1991) Nature 352:624-628; and MARLTS et al. 1991 J. Mol. Biol. 222:581-597.

Examples of ELISA techniques for identification and/or quantification of proteins include a 'sandwich ELISA', competitive ELISA or ELISPOT assay (ENGVALL et al. (1971) Immunochemistry 8:871-4; GOLDSBY et al. Enzyme-Linked Immunosorbent Assay. In: Immunology, 5th ed. (2003), pp. 148-150. W. H. FREEMAN, New York; WO 06/033974). ELISA assays may be adapted for use in microarray or chip methods (ANGENENDT et al. (2003) Anal. Chem 75:4368-4372).

Radioimmunoassay (RIA) may be used for quantifying an antigen, such as a protein, protein fragment or protein complex. Briefly, known quantities of a radioactive antigen is mixed with an antibody specific for the antigen, followed by mixing with unlabeled ('cold') antigen and measurement of the amount of labelled antigen that is displaced and free in the supernatant (YALOW et al. (1960) J Clin Invest 39:1157-75).

Gel electrophoresis may be used to separate a population of proteins, protein fragments or protein complexes on the basis of charge, molecular weight, shape, or a combination of these factors. For example aggregations may be separated by 'native' gel electrophoresis (BETTS et al. (1999) Methods Enzymol 309:333-50). Alternatively, a sample comprising proteins, protein fragments or protein complexes may be treated with detergents, denaturing, and/or reducing agents to reduce the effects of charge, aggregation and shape, so that molecular weight is the primary means of separation (LAEMMLI (1970) Nature 227:680). Once the proteins, protein fragments or protein complexes are separated in the gel, they may be transferred to a solid support for identification by an antibody-based method—the 'western' blot (TOWBIN et al. (1979) Proc. Natl Acad. Sci USA 76:4350; TOWBIN et al. (1989) J. Clin. Chem. Clin. Biochem 27:495). A variety of solid supports may be used, and a variety of detection methods are known, including colorimetric detection, chemiluminescence, radioactivity, fluorescence and the like. Several publications describe such methods and techniques in detail, and are described in KURIEN et al. (2003) J. Immunological Methods 274:1-15.

Affinity chromatography is a liquid chromatographic technique that makes use of a biological interaction for separation and analysis of a desired analyte (for example, a protein, protein fragment or protein complex) within a sample. For example, an affinity ligand ("bait") on a solid support selectively interacts, or "captures", a desired analyte in a liquid phase. The captured analyte may be subsequently eluted from the solid phase, or may be subjected to further analysis involving immunologic or non-immunologic methods, for example electrophoresis followed by western blot, ELISA, or mass spectrometry (HAGE (1999) Clin. Chemistry 45:593-615).

Protein microarrays generally use a 'bait and capture' assay design that may use an antibody as the 'bait' (as in an ELISA) or another affinity interaction with various proteins, compounds, cell extracts, etc, or a prepared surface (for example, charged, hydrophobic etc). The captured protein, protein fragment or protein complex may be detected by a variety of methods, such as fluorescence (BOENISCH (2001) Handbook Immunochemical Staining Methods. Dako, Carpinteria, Calif.; reviewed in ESPINA et al. (2004) J. Immunological Methods 290:122-133 and etc.).

Proteins, protein fragments or protein complexes may be detected in the context of a tissue using a tissue microarray (TMA) (KONONEN et al. (1998) Nature Medicine 4:844) and detection methods similar to those used in other microarrays may be used.

Label-free detection methods may include mass spectrometry, surface plasmon resonance (SPR) or atomic force microscopy (JOHNSSON et al. (1991) Anal. Biochem 198: 268; JONES et al. (1998) Anal. Chem 780:1233; BINNIG et al. (1986) Phys. Rev. Lett 56:930; LIOTTA et al. (2000) Nat. Rev. Genet. 1:480).

Mass spectrometry (MS) may be used in combination with ionization techniques such as electrospay ionization (ESI) or matrix-assisted laser desorption/ionization (MALDI) to identify proteins, protein fragments or protein complexes (KARAS et al. (1988) Anal. Chem. 60:2299-2310; HILLENKAMP et al. (1990); FENN et al. (1989) Science 246:64-71; and HILLENKAMP F. and KARAS M. Methods in Enzymol (1990) 193:280-295). Hybrid methods involving electrospray, time-of-flight mass spectrometer tandem mass analysis and the like may also be used to specifically identify proteins, protein fragments or protein complexes (SHEVCHENKO et al. (1997) Electrophoresis 18:2591-2600; MEDZIHRADSZKY et al. (2000) Anal Chem 72:552-558; BALDWIN et al. (2001) Anal. Chem 73:1707-1720; SHEVCHENKO et al. (2000) Anal Chem 72:2132-2141; U.S. Pat. No. 6,677,114; U.S. Pat. No. 6,906,320; U.S. Pat. No. 6,940,065; U.S. Pat. No. 6,508,986; U.S. Pat. No. 6,670,194).

Surface-enhanced laser desorption/ionization (SELDI) combines ionization techniques with affinity-binding of a population of protein or protein complexes to a solid support matrix. SELDI may be used in combination with mass spectrometry to provide specific identification of proteins, protein fragments or protein complexes (HUTCHENS et al. (1993) Rapid Commun Mass Spectrom 7:576-580; TANG et al. (2004) Mass Spectrom Rev 23:34-44).

MS or SELDI techniques may further be adapted for use in microarray or chip methods (see, for example, BERTONE et al. (2005) FEBS J. 272:5400-5411).

Various other publications known in the art address methods of separation and identification of proteins, protein fragments or protein complexes, for example LUEKING et al. (2005) Drug Discovery Today: Targets 10:789-794; NIELSEN et al. (2004) J. Immunological Methods 290:107-120; PANG et al. (2005) J Immunological Methods 302:1-12; PETRICOIN et al. (2003) J. Nutr 133:2476S-2484S; VISINTIN et al. (2004) J Immunological Methods 290:135-153.

3. Methods

Sample Collection

Mouse serum samples were collected by cardiac puncture and added to Beckton Dickinson serum separator tubes (Franklin Lakes, N.J.). Samples were allowed to clot for 30 minutes at room temperature and centrifuged for 15 minutes at 3000×g at room temperature. Samples were aliquoted immediately and stored at −80° C. Mouse plasma samples were collected by cardiac puncture, with sodium citrate added to 0.4%. Citrated samples were centrifuged for 15 minutes at 1500×g at 4° C. Human plasma and serum samples were collected by clean venipuncture using a 2 syringe technique, as described by PETZER (PETZER H. et al. (1988) Determination of human thrombin-antithrombin III complex in plasma with an enzyme linked immunosorbent assay. Thromb. Haemos. 59:101-106).

High Abundance Protein Depletion

Albumin, immunoglobulin, and transferrin were depleted from murine serum samples using a 100 mm Ms-3 Multiple Affinity Removal System (Agilent Technologies, Palo Alto, Calif.), according to the manufacturer's instructions. 4 age- and sex-matched pools of mouse serum samples were normalized for total protein to 12 mg/mL by diluting them in running buffer (Agilent Technologies). Each pool contained 6 independent serum samples. A KD Scientific syringe pump (Holliston, Mass.) was used to maintain a constant flow rate of 15 mL/h. 320 µL were subsequently used for high abundance protein depletion with identical pool collections obtained for all samples.

iTRAQ Analysis and iTRAQ Reagent Labelling

The depleted mouse serum samples were labelled with the iTRAQ reagent following the manufacturer's protocol (Applied Biosystems, Foster City, Calif.). Briefly, 100 µg of total protein from each of the 4 depleted serum pools was precipitated with acetone and resuspended in iTRAQ dissolution buffer for reduction, alkylation, and tryptic digestion. Each of the resulting peptide pools was then labelled with a different isotopic iTRAQ Reagent (114-117 Da) as follows: Idua+/+ mixed sex pool (114 Da), Idua−/− male pool (115 Da), Idua+/+ male pool (116 Da) and Idua−/− mixed sex pool (117 Da). The four differentially labelled pools were then combined and subjected to strong cation exchange (SCX) chromatography using a polysulfoethyl A column (Poly LC, Columbia, Md.). The combined sample was diluted in 10 mM KPO4 (pH 2.7), 25% ACN, applied to the column and peptides eluted over a 33 minute gradient to 35% 10 mM KH2PO4, 25% CAN, 0.5 M KCl with fractions collected at one minute intervals.

LC-MS/MS Analysis

The resulting 33 SCX fractions were then subjected to LC-MS/MS analysis utilizing a QStar Pulsar hybrid quadrupole-TOF instrument (Applied Biosystems) and an UltiMate micro HPLC (LC Packings, Sunnyvale, Calif.). The HPLC was equipped with a C18 PepMap guard column (LC Packings) separated from a C18 Pepmap Nano LC column (LC Packings) by a switching valve to allow for precolumn sample clean-up before switching inline for reversed phase chromatography and MS/MS analysis. Each SCX fraction was evaporated to dryness, resuspended in 5% ACN and 3% formic acid, and 25% of the sample was injected onto the C18 guard column in 98% water/acetonitrile (98:2), 0.05% formic acid (Buffer A) with the HPLC flowing to waste to remove sample contaminants. Following 10 minutes at 100 µl/ml, the guard column was switched inline with the C18 resolving column and mass spectrometer, and the peptides were eluted with a linear gradient to 60% water/acetonitrile (2:98), 0.05% formic acid (Buffer B) over 40 minutes. Following a 5 minute ramp to 80% Buffer B, the column was re-equilibrated in 98% buffer A for 15 minutes prior to the injection of the next SCX fraction.

Data Acquisition and Analysis

MS data was acquired automatically using Analyst QS 1.0 software Service Pack 8 (ABI MDS SCIEX, Concord, Canada). An information-dependent acquisition method consisting of a 1 second TOFMS survey scan of mass range 400-1200 atomic mass units and two 2.5 second product ion scans of mass range 100-1500 atomic mass units was utilized. The two most intense peaks over 20 counts, with charge state 2-5 were selected for fragmentation and a 6 amu window was used to prevent the peaks from the same isotopic cluster from being fragmented again. Once an ion was selected for MS/MS fragmentation it was put onto an exclusion list for 180 seconds. Following the initial data acquisition run (iTRAQ acquisition A), an exclusion list was created for all peptides identified with a confidence of 95% or greater in each of the SCX fractions. A second injection of each SCX fraction using the exclusion list for that fraction and the same LC and MS conditions as the first run was then performed in order to detect the lower concentration proteins present in plasma (iTRAQ acquisition B).

The resulting data files were combined and processed using the Interrogator™ algorithm in the ProQuant software (v1.0) (Applied Biosystems) in Analyst using the following parameters: The MS and MS/MS mass tolerances were set to 0.20. A rodent subset of the Celera Discovery Systems Database (01/24/2004) was used for searching. Methyl methanethiosulphonate (MMTS) modification of cysteines was used as a fixed modification. The number of missed cleavages was set to 1. All results were written to a Microsoft Access database and, to reduce redundancy, ProGroup Viewer version 1.0.5 (Applied Biosystems) was used to assemble and report the data. Protein % Confidence Scores, which are influenced by the closeness of the observed peptide spectrum to the predicted spectrum, the number of peptides identified for a given protein, as well as the variance of abundance of each peptide for the given protein, were used to calculate a Protein Score using the equation Protein Score=$-\log[1-(\text{Protein \% Confidence})/100]$.

Abundances of each identified protein in the sample pools were calculated based on the abundance of reporter tags bound to the peptide tryptic fragments for each pool. Where more than one peptide was identified for a protein, the abundance was calculated by weighted averaging of the abundance of the individual peptides including a 95% confidence interval. Protein abundances were adjusted for global labeling bias by a correction factor that assumed an average relative protein abundance of 1 across all samples. Relative abundances are determined by dividing the abundance of each protein from each pool by the corresponding protein in another pool. All proteins found to have significantly altered relative abundances were manually verified by inspecting the corresponding peptide matches.

Western Blotting

Western blot analysis was performed on 7.5% Tris-glycine gels and transferred to Pall (East Hills, N.Y.) BioTrace NT membranes. Anti-human HCII and anti-human antithrombin III antibodies were from Affinity Biologicals (Hamilton, ON). Membranes were blocked with 5% Carnation powdered skim milk, 0.05% PBS-T overnight at 4° C. Western blot analysis of human samples used primary antibody at a concentration of 1 µg/mL, with secondary antibody at a concentration of 1.3 µg/mL. Western blot analysis of mouse samples used 3 µg/mL primary antibody, and 1.3 µg/mL secondary antibody. Antibody incubations were performed for 60 minutes at room temperature. Proteins were detected with West Pico detection kits (Pierce, Rockford, Ill.) according to the manufacturer's instructions.

ELISA

HCII-T ELISA kits were obtained from Affinity Biologicals (Hamilton, ON) and used according to the manufacturer's instructions. This kit uses polyclonal sheep anti-human thrombin antibody for capture and peroxidase-conjugated polyclonal goat anti-human HCII antibody for detection. Standards were derived from purified human HCII and thrombin (Enzyme Research Laboratories, South Bend, Ind.) reacted in the presence of 0.05 U/mL heparin (Sigma, St. Louis, Mo.). MPS IH serum samples were diluted 500-fold and MPS IH/S samples were diluted 100-fold in factor II-depleted plasma (Affinity Biologicals) while control samples were undiluted. All standards and samples were tested in triplicate.

HCII-T ELISA Materials and Methods

Materials:
96 well plate—Immulon: 4 HBX
HCII-T kit—Affinity: T:HCII EIA (−20° C.)
Buffers—coating (20° C.), wash (4° C.), substrate (4° C.), blocking (−20° C.), diluent (−20° C.)
OPD Tablets (4° C.)—Sigma #P-6912
30% Peroxide (4° C.)—Fisher H325-100
General Purpose Serum Diluent (GP-SD1)—Immunochemistry Technologies #647

Day 1
1) Dilute 100 µL capture antibody in 10 mL coating buffer in a 15 mL falcon tube.
2) Apply 100 µL diluted antibody to all wells using multi-channel pipet; incubate 10 min @ RT, O/N @ 4° C.
3) Thaw diluent and blocking buffers O/N @ 4° C.; bring wash and substrate buffers to RT O/N.
4) Plan well assignments and samples.

Day 2
5) Bring diluent and blocking buffers to RT.
6) Label tubes for standard and sample dilutions.
7) Empty 96 well plate.
8) Apply 150 µL blocking buffer to all wells; incubate at least 90 min @ RT.
9) Add appropriate amount of TBS to all tubes before beginning dilutions.
10) Thaw 1 µM HCII-T standard (−80° C.) on ice; prepare standard dilutions as per table. Mix each solution very well before using it to make the following dilutions (see Dilution TABLE below). Refreeze stock 1 µM HCII-T standard immediately after use.

TABLE 4

DILUTIONS

| Stock standard solution | Volume standard (µL) | Volume serum diluent (µL) | Final standard concentration |
|---|---|---|---|
| 1 µM | 9 | 141 | 60 nM |
| 60 nM | 18 | 702 | 1500 pM |
| 60 nM | 12 | 708 | 1000 pM |
| 60 nM | 10 | 990 | 600 pM |
| 600 pM | 120 | 60 | 400 pM |
| 600 pM | 60 | 120 | 200 pM |
| 600 pM | 50 | 250 | 100 pM |
| 600 pM | 50 | 550 | 50 pM |
| 600 pM | 16 | 464 | 20 pM |
| 600 pM | 16 | 944 | 10 pM |
| 600 pM | 8 | 952 | 5 pM |

11) Dilute samples with the following dilution series:

TABLE 5

DILUTION SERIES

| Desired dilution factor (series) | First dilution (µL neat sample/µL GP-SD1) | Second dilution (µL first dilution/µL GP-SD1) |
|---|---|---|
| 2X | 40/40 | N/A |
| 5X | 16/64 | N/A |
| 10X | 8/72 | N/A |
| 50X | 8/392 | N/A |
| 100X | 8/792 | N/A |

TABLE 5-continued

DILUTION SERIES

| Desired dilution factor (series) | First dilution (μL neat sample/μL GP-SD1) | Second dilution (μL first dilution/μL GP-SD1) |
|---|---|---|
| 200X (100-2) | 8/792 | 400/400 |
| 250X (25-10) | 8/192 | 20/180 |
| 500X (50-10) | 8/392 | 50/450 |

12) Wash plate 4×5 min with wash buffer (150 μL/well).
13) During washes, aliquot 80 μL of each standard/sample into a 500 μL tube. Add 240 μL sample diluent into each tube. Mix well. Centrifuge momentarily @ 5000 rpm.
14) Apply 100 μL of standards and samples in triplicate to wells (for example a 96-well micro-titer plate). Apply 100 μL sample diluent to blank wells.
15) Incubate 2 hours @ RT
16) Wash plate 4×5 min with wash buffer. During washes, dilute 100 μL detecting antibody in 10 mL sample diluent in a 15 mL falcon tube.
17) Apply 100 μL diluted detecting antibody to each well; Incubate 60 min @ RT
18) Wash plate 4×5 min with wash buffer. During washes, dissolve one OPD tablet in 12 mL substrate buffer in a 15 mL falcon tube. Add 12 μL $H_2O_2$ to OPD solution during last wash to make OPD substrate. Mix well, but don't shake.
19) Apply 100 μL OPD substrate per well. Incubate for 10 min.
20) Quench reaction with 50 μL $H_2SO_4$ per well. Wait 10 minutes.
21) Read @ 490 nm, 0.1 sec on plate reader.

Standard Preparation:

React 1 μM purified human thrombin with 5 μM purified human HCII in 1×TBS containing 1 mM EDTA and 0.05 U/mL heparin at 37° C. for 30 minutes. Aliquot standard in 50 μL amounts and store at −80° C. Confirm reaction by SDS-PAGE.

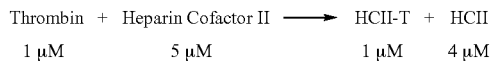

Thrombin + Heparin Cofactor II ⟶ HCII-T + HCII
1 μM        5 μM                      1 μM    4 μM Buffer Recipes:

| Coating buffer: | 50 mM carbonate - 1.59 g of $Na_2CO_3$ and 2.93 g of $NaHCO_3$; make to 1 L. Adjust pH to 9.6. Store at room temperature. |
|---|---|
| Blocking buffer: | PBS-BSA - 4.0 g NaCl, 10 g BSA (RIA grade), 100 mL 10X PBS; make to 1 L. Adjust pH to 7.4 with NaOH or $K_3PO_4$, if necessary. Aliquot in 35 mL amounts and store at −20° C. |
| Diluent: | HBS-T20-BSA - 11.90 g HEPES, 1.46 g NaCl, 5 g BSA, 0.5 mL Tween-20. Make to 500 mL. Adjust pH to 7.2 with NaOH. Aliquot in 35 mL amounts and store at −20° C. |
| Substrate buffer: | Citrate-phosphate buffer - 5.2 g citric acid, 13.8 g $Na_2HPO_4$. |
| OPD: | o-phenylenediamine - TOXIC! Dissolve 1 5 mg OPD tablet in 12 mL substrate buffer. Add 12 μL 30% $H_2O_2$. Make immediately before use; do not store. |
| Stopping solution: | 2.5 M $H_2SO_4$ - CAUTION: VERY CORROSIVE. Where stock solution is 18 M (37 N), add 13.9 mL to 86 mL $H_2O$. |
| Standard Rxn Buffer: | 1 mM EDTA, 0.05 U/mL heparin - 0.1861 g $Na_2EDTA\cdot2H_2O$, 1X TBS to 500 mL. Warm to 37° C. until EDTA dissolves. Add 139 μL 180 U/mL heparin. Mix well before using. Make fresh each time. |

4. Results

EXAMPLES

Example 1 iTRAQ Serum Proteomic Studies

Serum samples from normal and idua−/− mice were depleted of albumin, immunoglobulin, and transferrin using a 100 mm Ms-3 Multiple Affinity Removal System (Agilent Technologies, Palo Alto, Calif.) according to the manufacturer's instructions. 4 age- and sex-matched pools (Idua+/+ mixed sex pool, Idua+/+ male pool, Idua−/− mixed sex pool and Idua−/− male pool) of mouse serum samples from 6 animals were normalized for total protein to 12 mg/mL by diluting them in running buffer (Agilent Technologies). 320 μL were subsequently used for high abundance protein depletion with identical pool collections obtained for all samples. Pools were labeled with different isotopic iTRAQ reagents as described supra, and analyzed by LC-MS/MS analysis, as described herein.

Using a 94% Protein Confidence score cut-off applied to data observed over two cumulative MS/MS acquisitions, iTRAQ analysis resulted in the identification of 1701 distinct peptides belonging to 198 unique proteins (TABLE 6). 181 proteins were identified on the strength of two or more peptides, the majority of which were represented by at least 5 peptides (TABLE 7). This weighting toward 5+ peptides per protein is likely due to the dynamic range of protein concentrations in serum, where more abundant proteins can be expected to be identified by several peptides. The second MS/MS data acquisition resulted in a 30% increase in the total number of serum proteins identified.

TABLE 6 iTRAQ Summary Data

| Protein Confidence | iTRAQ Acquisition A | | | iTRAQ Acquisition A + B | | |
|---|---|---|---|---|---|---|
| Level, % | 94 | 95 | 99 | 94 | 95 | 99 |
| # of Peptides | 1132 | 1131 | 1048 | 1701 | 1686 | 1577 |
| # of Proteins | 151 | 150 | 114 | 198 | 195 | 150 |

TABLE 7

Number of unique peptides per protein in iTRAQ data collection, 94% Protein Confidence.

| | Number of Peptides/Protein | | | | | Total # of Proteins |
|---|---|---|---|---|---|---|
| | 1 | 2 | 3 | 4 | 5+ | |
| iTRAQ Acquisition A | 22 | 17 | 11 | 10 | 91 | 151 |
| iTRAQ Acquisition B | 17 | 21 | 30 | 16 | 114 | 198 |

To investigate intersample variation, the relative abundances observed in the Idua+/+ male pool to the Idua+/+ mixed sex pool as well as the Idua−/− male pool to the Idua−/− mixed sex pool at a 99% Protein Confidence level (FIG. 1A) were compared. The vast majority of proteins show no significant change in expression levels between like pools, with the exception of one outlier. The possibility of a sex-specific expression difference observed in the outlier (∼16-fold decreased) in the Idua+/+ Male:Idua+/+ Mixed sex comparison is eliminated by the absence of such a difference in the Idua−/− pools comparison and the decreased relative abundance of this protein (alpha-1-B glycoprotein) was assumed to be an artifactual in the Idua+/+ mixed sex control pool.

Comparison of the average protein relative abundances of the two Idua−/− pools with the Idua+/+ mixed sex pool reveals the variation between mutant and control pools is similar to that observed between like pools. However, a few proteins showed more extreme abundance differences (see FIG. 1A). This suggests there is minimal variation in protein quantities between the MPS and normal serum proteomes, with no single protein present at a dramatically different level.

In order to select a panel of proteins to be investigated as candidate MPS markers with significantly altered relative abundances in the Idua−/− serum proteome, the relative abundances of each protein in the two Idua−/− pools were averaged then tested for two factors. First, it was determined which proteins showed average relative abundances exceeding the 95% confidence intervals of the same proteins' abundances in the Idua+/+ male pool. Second, proteins that also showed average relative abundances with confidence intervals not overlapping 0.00 (on a logarithmic scale) were considered strong candidates. The Idua+/+ mixed sex pool was used as the denominator pool for both analyses. Combining these criteria selected proteins exceeding the natural variability of proteins in both the MPS and WT animals, regardless of the absolute value of the change. Candidate MPS markers selected by these criteria are indicated as red spots in FIG. 1A and listed in TABLE 8A. Candidate proteins with the most extreme deviation from the normal state were fibrinogen gamma (4.96-fold increased), fibrinogen alpha (2.20-fold increased), and heparin cofactor II (1.79-fold decreased). Elevated fibrinogen in mutant serum samples suggests impaired thrombin activity during clotting to form serum. 5 of the 17 proteins identified by iTRAQ with modified abundance in MPS I mice are serine protease inhibitors (TABLE 8A).

TABLE 8B

MPS Marker Protein Human Sequence Examples.

| Mouse Protein from TABLE 8A | Human Sequence Example | GenBank Accession No. for Human |
|---|---|---|
| Fibrinogen, γ-polypeptide | Fibrinogen Gamma Chain | AAB59531.1 |
| Fibrinogen, α-polypeptide | Fibrinogen Alpha Chain | AAI01936.1 |
| α-1-antitrypsin 1-5 | Alpha-1-antitrypsin | AAB59495.1 |
| Inter-α trypsin inhibitor, heavy chain 1 | Inter-alpha (globulin) Inhibitor H1 | NP_002206.1 |
| Apolipoprotein B | Apolipoprotein B Variant | BAD92083.1 |
| Pregnancy Zone Protein (Pzp) | Human Pregnancy Zone Protein | CAA38255.1 |
| Gelsolin | Gelsolin Isoform b | NP_937895.1 |
| Kininogen precursor | kininogen (KNG1) | AAH26253.1 |
| Histidine-rich glycoprotein | Histidine-rich Glycoprotein Precursor | NP_000403.1 |
| Alpha-1 proteinase inhibitor 2 | Alpha-1-Antitrypsin | AAA51546.1 |
| Apolipoprotein C-III | Apolipoprotein C-III | AAI21082.1 |
| Factor XIII beta | Coagulation Factor XIII, B Polypeptide | AAT85802.1 |
| Paraoxonase 1 | Paraoxonase 1 | EAL24133.1 |
| Heparin cofactor II | Heparin Cofactor II Precursor | NP_000176.2 |

Example 2

Heparin Cofactor II Western Blot Analysis in MPS I Mice and Humans

To investigate the HCII reduction in the serum of Idua−/− mice, western blot analysis was used utilizing goat anti-human HCII antibodies (data not shown). Surprisingly, the marked reduction in native HCII levels was also associated with the presence of a higher molecular weight protein only in the mutant animals' sera, consistent with the published size of the HCII-thrombin (HCII-T) complex (TOLLEFSEN D M et

TABLE 8A

Proteins with significantly altered relative abundance in the MPS mouse serum, Idua+/+ mixed sex denominator.

| GenBank Accession No. | Protein % confidence score rank | Protein | Log$_2$ of average relative abundance | Fold increase/ decrease | Biological function |
|---|---|---|---|---|---|
| AAH19506 | 95 | Fibrinogen, γ-polypeptide | 2.310 | +4.96 | Blood clotting |
| AAH05467 | 71 | Fibrinogen, α-polypeptide | 1.137 | +2.20 | Blood clotting |
| AAC28866 | 87 | α-1-antitrypsin 1-5 | 0.636 | +1.55 | Serine protease inhibitor |
| AAH13465 | 56 | Inter-α trypsin inhibitor, heavy chain 1 | 0.480 | +1.40 | Serine protease inhibitor |
| AAA37246 | 5 | Apolipoprotein B | 0.347 | +1.27 | Lipid and fatty acid transport |
| AAH57983 | 2 | Pregnancy Zone Protein (Pzp) | 0.154 | +1.11 | Serine protease inhibitor |
| AAH23143 | 29 | Gelsolin | −0.144 | −1.11 | Cytoskeletal protein |
| BAA19743 | 26 | Kininogen precursor | −0.281 | −1.22 | Protein metabolism and modification |
| BAB33095 | 31 | Histidine-rich glycoprotein | −0.309 | −1.24 | Biological process unclassified |
| AAC28865 | 23 | Alpha-1 proteinase inhibitor 2 | −0.377 | −1.30 | Serine protease inhibitor |
| AAH21776 | 102 | Apolipoprotein C-III | −0.386 | −1.31 | Lipid metabolism |
| AAH30166 | 90 | Factor XIII beta | −0.395 | −1.31 | Blood clotting |
| AAH12706 | 64 | Paraoxonase 1 | −0.414 | −1.33 | Peroxidase |
| AAH34543 | 78 | Heparin cofactor II | −0.840 | −1.79 | Serine protease inhibitor | al. (1982) Heparin cofactor II. Purification and properties of a heparin-dependent inhibitor of thrombin in human plasma, J. Biol. Chem. 257:2162-2169). Antibodies directed to thrombin confirmed that this was indeed HCII-thrombin complex. An elevation of serum HCII-T complex in serum samples from both severe and attenuated human cases of MPS I were compared to that of controls. Interestingly, the largest amounts of HCII-T complex were detected in the MPS IH patients (severe) in comparison to the MPS IH/S patient (attenuated). Western analysis also revealed no detectable HCII-T in plasma samples of Idua-/- or WT mice, nor in plasma samples from humans nor in serum controls from humans.

Example 3

Heparin Cofactor II Western Blot Analysis in Treated MPS I Patients

The level of HCII-T in a Hurler patient (12 months old) receiving enzyme replacement therapy (ERT) preceding and following bone marrow transplantation (BMT), and one Hurler-Scheie patient (8 years old) undergoing ERT only were also examined using westernblots. Enzyme treatment in the Hurler patient (data not shown) did not normalize HCII-T levels, but significantly reduced the amount of HCII-T levels to that seen in the attenuated patient studied and as compared to pre-treatment levels. Further reduction in HCII-T occurred following bone marrow transplantation (between 36 and 52 weeks and as measured at 52 weeks from the start of treatment). Although this patient was well engraphed by week 52, she subsequently died of pulmonary hemorrhage. The Hurler-Scheie patient also showed marked reduction of HCII-T early during ERT treatment as compared to pre-treatment levels, but then subsequently developed detectable HCII-T complex later during treatment (at 24 weeks and 80 weeks), with little or no detectable HCII-T at 3, 5.5, 16, 36 and 48 weeks.

Example 4

HCII-T ELISA Analysis

TABLE 9 illustrates the dramatic elevation of HCII-T in the serum of MPS 1H and MPS IH/S patients as well as murine MPS I samples in comparison to controls. MPS IH patients' serum HCII-T complex levels ranged from 174,700-208,600 pM, with an average value of 188,600 pM, representing a 630-fold increase relative to controls. The serum sample from a MPS IH/S patient had a HCII-T concentration of 46,000 pM (154-fold increase), reflective of his attenuated phenotype.

In contrast to the lack of detectable complex by western blot, ELISA revealed that plasma HCII-T levels were increased in MPS patients and the MPS I mouse, with the minimum concentration of HCII-T complex in MPS IH patients exceeding the maximum control value by 68%. The ELISA data in EXAMPLE 4 differed only slightly from the protocol described above with regards to the dilutions used.

TABLE 9

| | HCII-T ELISA | |
| --- | --- | --- |
| Sample (age in brackets) | Serum [HCII-T] (pM ± SD) | Plasma [HCII-T] (pM ± SD) |
| Control (10 yr F) | 115.1 | 17.92 |
| Control (10 yr M) | 398.0 | 9.91 |

TABLE 9-continued

| | HCII-T ELISA | |
| --- | --- | --- |
| Sample (age in brackets) | Serum [HCII-T] (pM ± SD) | Plasma [HCII-T] (pM ± SD) |
| Control (30 yr M) | 384.7 | 6.27 |
| MPS 1H (10 mo, Patient A) | 174 700 | 30.15 |
| MPS 1H (12 mo, Patient B) | 182 400 | Not tested |
| MPS 1H (14 mo, Patient C) | 208 600 | 98.37 |
| MPS 1H/S (8 yr, Patient D) | 46 000 | Not tested |
| Idua$^{+/+}$ (n = 5) | 75.46 ± 4.99 | 3.77 ± 1.20 |
| Idua$^{-/-}$ (n = 3) | 628.1 ± 163.2 | 79.50 ± 38.9 |

Significantly decreased levels of the serine protease inhibitor (SERPIN), heparin cofactor II (HCII) is present in MPS-affected animals. Although native HCII levels are reduced, there is marked HCII-thrombin (HCII-T) complex elevation in MPS-affected animals. Translation of these findings to humans with MPS I show equivalent findings. Importantly, in humans the elevation of HCII-T complex appears to be correlated to disease severity and is responsive to treatment. These results indicate that HCII-T is an excellent MPS markers for MPS I.

In addition, the level of HCII-T complex correlates with the clinical measures of disease severity as well as responsiveness to therapy. Furthermore, patients undergoing ERT and/or BMT maintain residual amounts of serum HCII-T.

Example 5

Expanded HCII-T ELISA Serum Analysis

Figure 2:
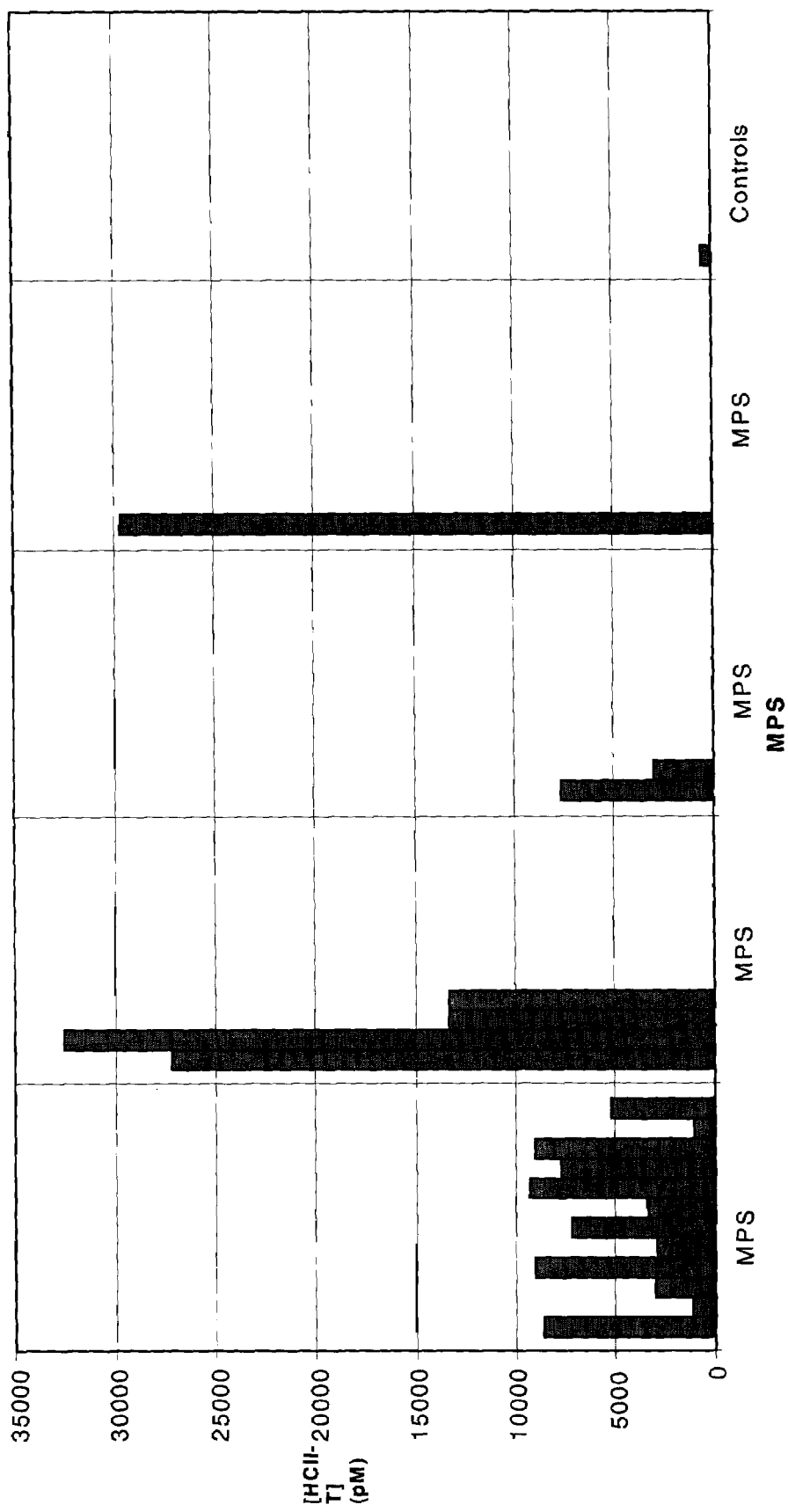
FIG. 2 shows a plot of serum HCII-T levels (pM) in individual subjects with a variety of MPSs as compared to a control mean of 5463 pM (n=43) as also shown in TABLE 10.

Additional HCII-T ELISAs of MPS serum were carried out and compared to control HCII-T levels. As shown in TABLE 10 and in FIG. 2, there is a graded response between attenuated subjects (MPS IH/IS) and severe subjects (MPS IH). Furthermore, it should be noted that the mean control (5,463 pM) and the highest control value for HCII-T (13,500 pM) is still well below the most attenuated MPS HCII-T levels.

TABLE 10

SERUM HCII-T levels (pM) in individual subjects with a variety of MPS types as compared to controls (mean 5463 pM).

| MPS IH/IS | MPS IH | MPS II | MPS IIIA | MPS IIIB | Control (n = 43) |
| --- | --- | --- | --- | --- | --- |
| 17,217 | 188,621 | 208,000 | 81,474 | 246,183 | 5,463* |
| 25,535 | 205,565 | | | | |
| 100,231 | 133,117 | | | | |
| 20,670 | 133,512 | | | | |
| 37,783 | | | | | |
| 23,890 | | | | | |
| 33,727 | | | | | |
| 24,961 | | | | | |
| 71,033 | | | | | |
| 17,059 | | | | | |
| 32,963 | | | | | |
| 85,645 | | | | | |

*mean of 43 control subjects with a range of 895 pM to 13,500 pM.

Example 6

HCII-T ELISA Serum Analysis of Patients Undergoing Enzyme Replacement Therapy (ERT) and Bone Marrow Transplant (BMT)

Figure 3A:
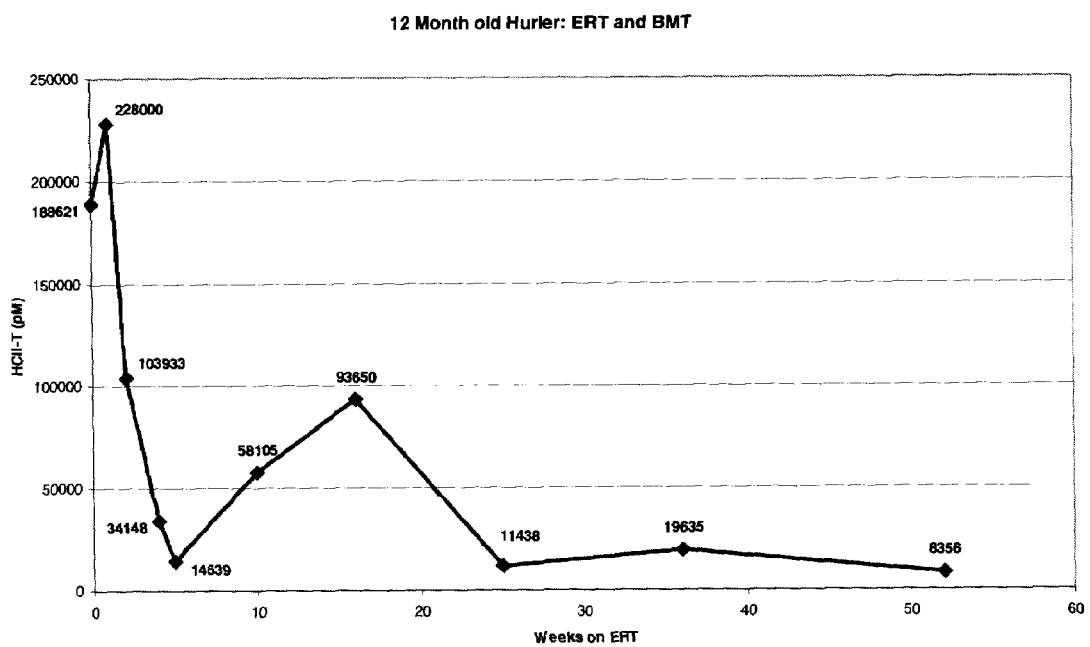
FIG. 3A shows serum HCII-T levels are responsive to treatment by enzyme replacement in a MPS I patient, providing serum HCII-T levels in a 12 month old child with MSP I (hurler syndrome) who received Aldurazyme (ERT) weekly from time 0 through to week 53 with a bone marrow transplantation performed at week 35. Control Normal values: Mean 5463 SD 3479 pM

Serum HCII-T levels are responsive to treatment by enzyme replacement in MPS I (as shown in FIG. 3A). The serum HCII-T levels are shown for a 12 month old child with MSP IH (Hurler syndrome), who received Aldurazyme (ERT) weekly from time 0 through to week 53 and a bone marrow was transplantation performed at week 35 (Control Normal values: Mean 5463 SD 3479 pM).

Figure 3B:
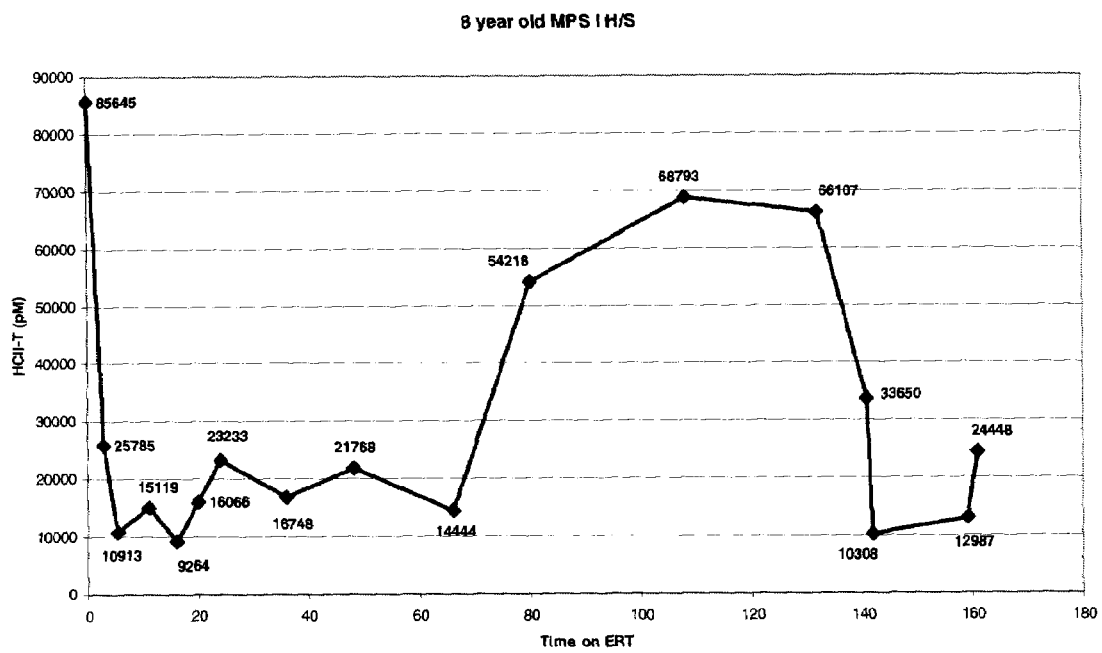
FIG. 3B shows serum HCII-T levels are responsive to treatment by enzyme replacement in a MPS I patient, providing serum HCII-T levels in an 8 year old child with MSP I (Hurler/Scheie syndrome) who received Aldurazyme (ERT) weekly from time 0 through to week 162. Control Normal values: Mean 5463 SD 3479 pM.

Serum HCII-T levels are also shown to be responsive to treatment by enzyme replacement in MPS I (as shown in FIG. 3B). The serum HCII-T levels are shown for an 8 year old child with MSP I (Hurler/Scheie syndrome) who received Aldurazyme (ERT) weekly from time 0 through to week 162. It is speculated that the spike in HCII-T between week 60 and week 140 may be due to the dosing of the enzyme or due to the patient being Aldurazyme antibody positive (Control Normal values: Mean 5463 SD 3479 pM). Nevertheless, the plot demonstrates the sensitivity of the assay and the usefulness to follow subjects on a treatment regimen.

Example 7

Antithrombin III-Thrombin (ATIII-T) Serum ELISAs

Antithrombin III (ATIII) is a principle circulating SERPIN, present at approximately twice the plasma concentration as compared to HCII, and is known to be activated by heparan sulphate. However, a comparison of serum levels of ATIII-T complex in MPS I patients shows no difference between controls and MPS patients (see TABLE 11 below). Accordingly, the data suggests that the use of the ATIII-T complex as an MPS marker is not promising.

TABLE 11

| Serum AntithrombinIII-T complex levels (pM) | | |
| --- | --- | --- |
|  | controls (n = 43) | MPS I (n = 15) |
| average | 554 | 478 |
| SD | 170 | 89 |
| low | 101 | 317 |
| high | 964 | 601 |
| *MPS II |  | 432 |
| *MPS IIIA |  | 529 |
| *MPS IIIB |  | 381 |

*MPS II/IIIA/IIIB single readings (not as above for MPS I and controls)

What is claimed is:

1. A method of identifying a compound that promotes glycosaminoglycan (GAG) degradation, the method comprising:
   (1) (a) providing a cell having reduced enzyme activity resulting in accumulation of undegraded or partially degraded GAGs, wherein the enzyme is involved in degrading GAGs and contacting the cell with one or more test compounds; or
   (b) providing a mucopolysaccharidoses (MPS) experimental animal having reduced enzyme activity resulting in an accumulation of undegraded or partially degraded GAGs and administering to the experimental animal one or more test compounds; and
   (2) determining whether there is a relative increase or decrease of MPS marker as a result of the administration of one or more test compounds,
   whereby any compound that promotes GAG degradation is identified.

2. The method of claim 1, wherein MPS marker is selected from one or more of the following markers:
   Fibrinogen, γ-polypeptide; Fibrinogen, α-polypeptide; α-1-antitrypsin 1-5;
   Inter-α trypsin inhibitor, heavy chain 1;
   Apolipoprotein B;
   Pzp protein; Gelsolin;
   Kininogen precursor;
   Histidine-rich glycoprotein;
   Alpha-1 proteinase inhibitor 2;
   Apolipoprotein C-III; Factor XIII beta;
   Paraoxonase 1;
   Heparin cofactor II thrombin complex (HCII-T); and
   Heparin cofactor II (HCII).

3. The method of claim 2, wherein the one or more test compounds increases HCII levels, or wherein the one or more test compounds decreases HCII-T levels.

4. The method of claim 1, further comprising administering any identified compound to a test subject.

5. The method of claim 1, further comprising incorporating any identified compound into a medicament.

6. A method for identifying an individual having mucopolysaccharidoses (MPS), or determining whether an individual is at risk for MPS, the method comprising:
   testing at least one biological sample from the individual in an MPS marker detection assay, operable for determining relative MPS marker levels, wherein an MPS marker level different from the MPS marker level in a normal subject is indicative of MPS status.

7. The method of claim 6, wherein MPS marker is selected from one or more of the following:
   Fibrinogen, γ-polypeptide; Fibrinogen, α-polypeptide; α-1-antitrypsin 1-5;
   Inter-α trypsin inhibitor, heavy chain 1;
   Apolipoprotein B;
   Pzp protein; Gelsolin;
   Kininogen precursor;
   Histidine-rich glycoprotein;
   Alpha-1 proteinase inhibitor 2;
   Apolipoprotein C-III;
   Factor XIII beta;
   Paraoxonase 1;
   Heparin cofactor II thrombin complex (HCII-T), and
   Heparin cofactor II (HCII).

8. The method of claim 6, wherein the MPS marker is HCII, and a decreased HCII level is indicative of MPS, or
   wherein the MPS marker is HCII-T, and an increased HCII-T level is indicative of MPS.

9. The method of claim 6, further comprising administering a treatment to the subject identified as having MPS or at risk for MPS.

10. The method of claim 9, wherein the treatment comprises Aldurazyme® (laronidase) administration.

11. The method of claim 9, wherein the treatment comprises a bone marrow transplant.

12. The method of claim 9, wherein the biological sample is collected one or more times prior to, during or after treatment.

* * * * *